United States Patent
Johnston et al.

(10) Patent No.: US 11,360,086 B2
(45) Date of Patent: Jun. 14, 2022

(54) DIAGNOSTIC TO DISTINGUISH BACTERIAL INFECTIONS

(71) Applicant: ARIZONA BOARD OF REGENTS ON BEHALF OF ARIZONA STATE UNIVERSITY, Scottsdale, AZ (US)

(72) Inventors: Stephen Johnston, Tempe, AZ (US); Lu Wang, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/896,117

(22) Filed: Jun. 8, 2020

(65) Prior Publication Data

US 2021/0041436 A1 Feb. 11, 2021

Related U.S. Application Data

(63) Continuation of application No. 16/480,887, filed as application No. PCT/US2018/016185 on Jan. 31, 2018, now Pat. No. 10,712,342.

(60) Provisional application No. 62/452,825, filed on Jan. 31, 2017.

(51) Int. Cl.
*G01N 33/53* (2006.01)
*G01N 33/569* (2006.01)

(52) U.S. Cl.
CPC ............ *G01N 33/56911* (2013.01); *G01N 33/56983* (2013.01); *G01N 2469/20* (2013.01)

(58) Field of Classification Search
CPC ............................................. G01N 33/56911
See application file for complete search history.

(56) References Cited

U.S. PATENT DOCUMENTS

| | | | |
|---|---|---|---|
| 8,796,414 B2 | 8/2014 | Johnston | |
| 8,969,255 B2 | 3/2015 | Johnston | |
| 9,309,298 B2 | 4/2016 | Johnston | |
| 9,482,666 B2 | 11/2016 | Domenyuk | |
| 9,709,558 B2 | 7/2017 | Johnston | |
| 9,732,131 B2 | 8/2017 | Johnston | |
| 9,757,472 B2 | 9/2017 | Diehnelt | |
| 9,766,239 B2 | 9/2017 | Gupta | |
| 9,863,938 B2 | 1/2018 | Johnston | |
| 9,970,932 B2 | 5/2018 | Woodbury | |
| 10,006,919 B2 | 6/2018 | Woodbury | |
| 10,011,649 B2 | 7/2018 | Diehnelt | |
| 10,046,293 B2 | 8/2018 | Woodbury | |
| 10,125,167 B2 | 11/2018 | Diehnelt | |
| 10,126,300 B2 | 11/2018 | Johnston | |
| 10,416,174 B1 | 9/2019 | Johnston | |
| 10,422,793 B2 | 9/2019 | Johnston | |
| 2004/0031072 A1 | 2/2004 | La Rosa et al. | |
| 2007/0271630 A1 | 11/2007 | Boukharov et al. | |
| 2008/0260763 A1 | 10/2008 | Felgner et al. | |
| 2009/0186042 A1 | 7/2009 | Johnston | |
| 2011/0143953 A1 | 6/2011 | Johnston et al. | |
| 2012/0021967 A1 | 1/2012 | Johnston et al. | |
| 2012/0065123 A1 | 3/2012 | Johnston et al. | |
| 2012/0094271 A1 | 4/2012 | Fu | |
| 2012/0190566 A1 | 7/2012 | Lindquist et al. | |
| 2012/0190574 A1 | 7/2012 | Johnston | |
| 2012/0220540 A1 | 8/2012 | Johnston et al. | |
| 2012/0316078 A1 | 12/2012 | Sykes | |
| 2013/0224730 A1 | 8/2013 | Johnston | |
| 2014/0087963 A1 | 3/2014 | Johnston | |
| 2014/0128280 A1 | 5/2014 | Johnston et al. | |
| 2015/0241420 A1 | 8/2015 | Johnston | |
| 2017/0131276 A1 | 5/2017 | Johnston | |
| 2017/0334963 A1 | 11/2017 | Johnston | |
| 2017/0343541 A1 | 11/2017 | Johnston | |
| 2018/0259510 A1 | 9/2018 | Woodbury | |
| 2018/0275136 A1 | 9/2018 | Woodbury | |
| 2018/0284114 A1 | 10/2018 | Johnston | |
| 2019/0194358 A1 | 6/2019 | Johnston | |
| 2019/0234962 A1 | 8/2019 | Johnston | |
| 2019/0271692 A1 | 9/2019 | Johnston | |

FOREIGN PATENT DOCUMENTS

| | | |
|---|---|---|
| WO | 2007101227 A2 | 9/2007 |
| WO | 2007101227 A8 | 9/2007 |
| WO | 2008048970 A2 | 4/2008 |
| WO | 2008048970 A8 | 4/2008 |
| WO | 2009126718 A2 | 10/2009 |
| WO | 2009140039 A2 | 11/2009 |
| WO | 2010027642 A2 | 3/2010 |
| WO | 2010028214 A2 | 3/2010 |
| WO | 2010059958 A2 | 5/2010 |

(Continued)

OTHER PUBLICATIONS

Altschul, S.F. et al, Gapped BLAST and PSI-BLAST: a new generation of protein database search programs. Nucleic acids research 25, 3389-3402 (1997).

Bailey, T.L. et al, Fitting a mixture model by expectation maximization to discover motifs in biopolymers (1994).

Bailey, T.L. et al, Meme Suite: tools for motif discovery and searching. Nucleic Acids Res 37, W202-208 (2009); published online EpubJul (10.1093/nar/gkp335).

Begitt, A. et al, STAT1-cooperative DNA binding distinguishes type 1 from type 2 interferon signaling. Nature Immunology 15, 168-176 (2014); published online EpubFeb (10.1038/ni.2794).

Boone, S.A. et al, Significance of fomites in the spread of respiratory and enteric viral disease. Applied and environmental microbiology 73, 1687-1696 (2007); published online EpubMar (10.1128/AEM.02051-06).

(Continued)

*Primary Examiner* — Albert M Navarro
(74) *Attorney, Agent, or Firm* — Knobbe, Martens, Olson & Bear, LLP

(57) ABSTRACT

Assays, arrays, and methods for distinguishing a bacterial infection from a viral infection are disclosed. The antibiotic crisis is in part driven by over prescription of antibiotics. There is a tendency, particular in pediatrics, to give an antibiotic even for viral infections. Thus, embodiments herein are directed to the problem of distinguishing a bacterial infection from a viral infection to reduce unnecessary antibiotic usage.

20 Claims, 8 Drawing Sheets

Specification includes a Sequence Listing.

(56) References Cited

FOREIGN PATENT DOCUMENTS

| | | | |
|---|---|---|---|
| WO | 2010111299 A2 | 9/2010 |
| WO | 2011029008 A2 | 9/2010 |
| WO | 2010148365 A2 | 12/2010 |
| WO | 2012134416 A2 | 10/2012 |
| WO | 2013067160 A2 | 5/2013 |
| WO | 2013077982 A1 | 5/2013 |
| WO | 2014036312 A2 | 3/2014 |
| WO | 2014036312 A8 | 3/2014 |
| WO | 2014039718 A1 | 3/2014 |
| WO | 2014039718 A8 | 3/2014 |
| WO | 2014062981 A1 | 4/2014 |
| WO | 2014062981 A9 | 4/2014 |
| WO | 2014144383 A1 | 9/2014 |
| WO | 2014145123 A2 | 9/2014 |
| WO | 2014165240 A1 | 10/2014 |
| WO | 2015031268 A1 | 3/2015 |
| WO | 2015095136 A1 | 6/2015 |
| WO | 2017059239 A1 | 4/2017 |
| WO | 2018223092 A1 | 12/2018 |
| WO | 2018223093 A1 | 12/2018 |
| WO | 2018223094 A1 | 12/2018 |
| WO | 2019055618 A1 | 3/2019 |
| WO | 2019143712 A2 | 7/2019 |

OTHER PUBLICATIONS

Chase, B.A. et al, Evaluation of biological sample preparation for immunosignature-based diagnostics. Clinical and Vaccine Immunology 19, 352-358 (2012).
Cox, N. et al, Global epidemiology of influenza: past and present. Annual review of medicine 51, 407-421 (2000).
Davies, J. et al, Origins and evolution of antibiotic resistance. Microbiology and molecular biology reviews : MMBR 74, 417-433 (2010); published online EpubSep (10.1128/MMBR.00016-10).
O'donnell, B. et al, Time-Frequency Analysis of Peptide Microarray Data: Application to Brain Cancer Immunosignatures. Cancer Informatics, 219-233 (2015); published online Epub06/18 (10.4137/CIN. S17285).
The White House. Executive Order—Combating Antibiotic-Resistant Bacteria (2014 www.whitehouse.gov/thepress-office/2014/09/18/executive-order-combating-antibiotic-resistant-bacteria).
Kollef M.H., Broad-spectrum antimicrobials and the treatment of serious bacterial infections: getting it right up front. Clinical infectious diseases : an official publication of the Infectious Diseases Society of America 47 Suppl 1, S3-13 (2008); published online EpubSep 15 (10.1086/590061).
Legutki, J.B. et al, Immunosignatures can predict vaccine efficacy. Proceedings of the National Academy of Sciences, (2013); published online Epub Oct. 28, 2013 (10.1073/pnas.1309390110).
Navalkar, K.A. et al, Application of immunosignatures to diagnosis of Valley Fever. Clinical and Vaccine Immunology in press, (2014).
Navalkar, K.A. et al, Peptide based diagnostics: Are random-sequence peptides more useful than tiling proteome sequences? Journal of Immunological Methods 417, 10-21 (2015); published online Epub2// (http://dx.doi.org/10.1016/i.jim.2014.12.002).
Oved, K. et al, A novel host-proteome signature for distinguishing between acute bacterial and viral infections. PloS one 10, e0120012 (2015)10.1371/journal.pone.0120012).
Restrepo, L. et al, Application of immunosignatures to the assessment of Alzheimer's disease. Annals of Neurology, 286-295 (2011)doi:10.1002/ana.22405).
Restrepo, L. et al, Feasibility of an early Alzheimer's disease immunosignature diagnostic test. Journal of Neuroimmunology, (2012)doi: 10.1016/j.jneuroim.2012.09.014).
Shallcross, L.J. et al, Antibiotic overuse: a key driver of antimicrobial resistance. The British journal of general practice : the journal of the Royal College of General Practitioners 64, 604-605 (2014); published online EpubDec (10.3399/bjgp14X682561).
Smialowski, P. et al, Pitfalls of supervised feature selection. Bioinformatics 26, 440-443 (2010); published online EpubFeb 1 (10.1093/bioinformatics/btp621).
Spellberg, B. et al. Infectious Diseases Society of, The epidemic of antibiotic-resistant infections: a call to action for the medical community from the Infectious Diseases Society of America. Clinical infectious diseases : an official publication of the Infectious Diseases Society of America 46, 155-164 (2008); published online Epub Jan. 15 (10.1086/524891).
Stafford, P. et al, General assessment of humoral activity in healthy humans. Molecular & Cellular Proteomics 15, 1610-1621 (2016).
Stafford, P. et al, Immunosignature system for diagnosis of cancer. Proceedings of the National Academy of Sciences 111, E3072-E3080 (2014).
Stafford, P. et al, Physical characterization of the "immunosignaturing effect". Molecular & cellular proteomics : MCP 11, M111 011593 (2012); published online Epub April (10.1074/mcp.M111. 011593).
Sweeney, T.E. et al, Robust classification of bacterial and viral infections via integrated host gene expression diagnostics. Science Translational Medicine 8, 346ra391-346ra391 (2016).
Tsalik, E.L. et al, Host gene expression classifiers diagnose acute respiratory illness etiology. Science translational medicine 8, 322ra311-322ra311 (2016).
Xu, G.J. et al, Viral immunology. Comprehensive serological profiling of human populations using a synthetic human virome. Science 348, aaa0698 (2015); published online Epub Jun. 5 (10.1126/science.aaa0698).
U.S. Appl. No. 16/562,383, filed Sep. 5, 2019, Johnston et al.
U.S. Appl. No. 16/568,076, filed Sep. 11, 2019, Johnston et al.
U.S. Appl. No. 16/617,805, filed Nov. 27, 2019, Johnston et al.
U.S. Appl. No. 16/617,830, filed Nov. 27, 2019, Johnston et al.
U.S. Appl. No. 16/617,889, filed Nov. 27, 2019, Johnston et al.
U.S. Appl. No. 16/748,723, filed Jan. 21, 2020, Woodbury et al.
UniProtKB_A0A0B2AQ09, Histidine kinase, Accession No. A0A0B2AQ09. Last Modified: Mar. 4, 2015. [online]. [Retrieved on Jul. 25, 2018]. Retrieved from the Internet: <URL:https ://www.uniprot.org/uniprot/A0AOB2A Q09> Protein; and Sequence (318 a.a.), the region between amino acid residues 14-29.
UniProtKB_U5H788, Uncharacterized protein. Accession No. U5H788 Last Modified: Dec. 11, 2013. [online]. [Retrieved on Jul. 25, 2018]. Retrieved from the Internet: <URL : https://www.uniprot.org/un iprotJU5H788> Protein; and Sequence (701 a.a.), the region between amino acid residues 570-584.
UniProtKB_D8U9M2, Uncharacterized protein. Accession No. D8U9M2. Last Modified: Oct. 5, 2010. [online]. [Retrieved on Jul. 25, 2018]. Retrieved from the Internet: <URL:https:f/www.uniprot.org/uniprot/D8U9M2> Protein; and Sequence (1141 a.a.), the region between amino acid residues 917-924, which is 100% identical to the region between amino acid residues 8-15 of the claimed Seq ID No. 2, and is 100% identical to the claimed Seq ID No. 4.
Ruwona et al., "Optimization of peptide arrays for studying antibodies to hepatitis C virus continuous epitopes", Journal of Immunological Methods, 2014, vol. 402(1-2), p. 35-42, PDF File: pp. 1-15.
Reineke et al., "Antibody epitope mapping using SPOT peptide arrays", Methods of Molecular Biology, 2009, vol. 524. pp. 145-167.
Patent Cooperation Treaty, International Searching Authority, International Search Report and Written Opinion for PCT/US2018/016185, 22 pages, dated Sep. 27, 2018.

SEQUENCE LISTING

```
<160> NUMBER OF SEQ ID NOS: 5

<210> SEQ ID NO 1
<211> LENGTH: 17
<212> TYPE: PRT
<213> ORGANISM: Artificial Sequence
<220> FEATURE:
<223> OTHER INFORMATION: SYNTHETIC

<400> SEQUENCE: 1

Gly Ala Leu Ser Arg Ser Phe Ala Asn Val Ser Phe Pro Gly Val Ala
1               5                   10                  15

Gly

<210> SEQ ID NO 2
<211> LENGTH: 17
<212> TYPE: PRT
<213> ORGANISM: Artificial Sequence
<220> FEATURE:
<223> OTHER INFORMATION: SYNTHETIC
```

-continued

```
<400> SEQUENCE: 2

Gly Leu Ser Asn Gly Ala Ser Ser Phe Gly Lys Ala Ser Gly Val Ala
1               5                   10                  15

Leu

<210> SEQ ID NO 3
<211> LENGTH: 6
<212> TYPE: PRT
<213> ORGANISM: Artificial Sequence
<220> FEATURE:
<223> OTHER INFORMATION: SYNTHETIC

<400> SEQUENCE: 3

Arg Ser Phe Ala Asn Val
1               5

<210> SEQ ID NO 4
<211> LENGTH: 8
<212> TYPE: PRT
<213> ORGANISM: Artificial Sequence
<220> FEATURE:
<223> OTHER INFORMATION: SYNTHETIC

<400> SEQUENCE: 4

Ser Phe Gly Lys Ala Ser Gly Val
1               5

<210> SEQ ID NO 5
<211> LENGTH: 6
<212> TYPE: PRT
<213> ORGANISM: Artificial Sequence
<220> FEATURE:
<223> OTHER INFORMATION: SYNTHETIC

<400> SEQUENCE: 5

Leu Ser Asn Gly Ala Ser
1               5
```

DIAGNOSTIC TO DISTINGUISH BACTERIAL INFECTIONS

CROSS-REFERENCE TO RELATED APPLICATIONS

This application is a continuation of U.S. application Ser. No. 16/480,887, filed Jul. 25, 2019, which represents the national stage entry of PCT International Application No. PCT/US2018/016185, filed on Jan. 31, 2018, and is based on, and claims a priority benefit from—U.S. Provisional Patent Application No. 62/452,825, filed Jan. 31, 2017, and entitled "Diagnostic to Distinguish Bacterial Infections," each of which is incorporated herein by reference in its entirety.

STATEMENT REGARDING FEDERALLY SPONSORED RESEARCH OR DEVELOPMENT

This invention was made with government support under HSHQDC-15-C-B0008 awarded by the Department of Homeland Security, Science and Technology. The government has certain rights in the invention.

REFERENCE TO A SEQUENCE LISTING SUBMITTED VIA EFS-WEB

The content of the ASCII text file of the sequence listing named "112624_00954_ST25.txt" which is 1.25 kb in size was created on Jan. 31, 2018 and electronically submitted via EFS-Web herewith the application is incorporated herein by reference in its entirety.

BACKGROUND

Antibiotic resistance is a global problem mainly due to the overuse of antibiotics in clinical settings. Overuse is mainly caused by the lack of accurate diagnosis that can distinguish bacterial infections from other types of infections. This is especially true for respiratory tract infections and pediatric sepsis. More accurate diagnosis at the time of an initial clinical visit that can distinguish bacterial from other infections would greatly curb the antibiotic overuse problem.

A major advance in stemming the antibiotic crisis would be to have a diagnostic that could readily distinguish a bacterial from viral infection on presentation with symptoms. This would decrease the unnecessary use of antibiotics while still allowing their application optimally for bacterial infections. Current research on distinguishing bacterial from viral infections has mostly been focusing on genome-wide expressions (GWAS). The notion is that gene expression will change upon infections of different pathogens. However, a serological test detection method for pathogens is antibody response. There are many complicating factors that make analysis of antibodies between viral and bacterial infections complex—one of the most important is the study platform.

SUMMARY

Embodiments of the current disclosure describe an array and methods for distinguishing a bacterial infection from a viral infection. In certain embodiments, the array comprises two peptides, which first peptide comprises SEQ ID NO.1 and said second peptide comprises SEQ ID NO.2. Further, the first peptide comprises a motif able to be bind to a plurality of bacterial specific antibodies, wherein the motif comprises SEQ ID NO.3 and the second peptide comprises a first motif and a second motif able to be bind to a plurality of bacterial specific antibodies, wherein the first motif comprises SEQ ID NO.4 and the second motif comprises SEQ ID NO.5.

In certain embodiments, a method to distinguish a bacterial infection from a viral infection is disclosed. The method contains the steps of contacting an antibody-containing sample with an array of immobilized peptides, wherein said peptides are selected from a group consisting of one or more peptides that bind to antibodies produced in response to a bacterial infection and one or more peptides that bind to antibodies produced in response to a viral infection; and detecting binding of an antibody from said sample with a peptide from said group.

BRIEF DESCRIPTION OF DRAWINGS

Embodiments of the invention will be better understood from a reading of the following detailed description taken in conjunction with the drawings in which like reference designators are used to designate like elements, and in which.

Figure 1:
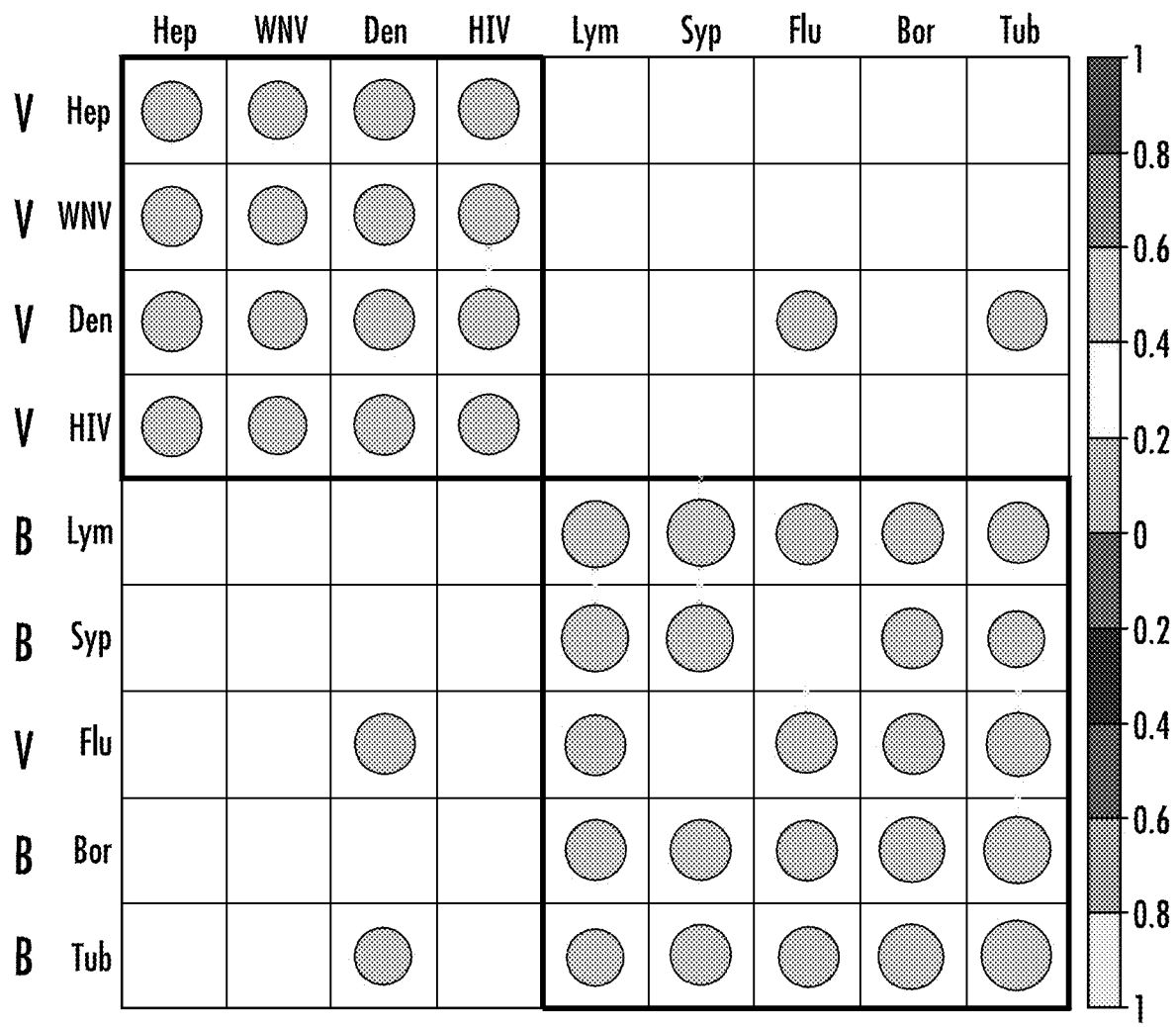
FIG. 1. Hierarchical clustering for the correlation of the whole immunosignature by type of infection shows potential classification of bacterial versus viral infection. Correlation is calculated for each pair-wise sample comparison, then the samples that belong to the same class are averaged to a single correlation value. The clustering table shows most viruses can be distinguished from the bacteria, with the exception of flu.

Color is true label. All samples are included in this figure. Graph shows good separation between the two groups.

DETAILED DESCRIPTION

Embodiments of the disclosure are described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Immunosignature is a peptide microarray that derives peptide sequences from random space rather than biological sequence space. The analysis of semi-random sequences allows for a mostly unbiased search for antibodies that may display a common binding motif. The applicant would not focus on sequences for any given pathogen, which allows exploring more broadly for antibodies that may fall into a pattern that overlaps bacteria and virus.

The immunosignatures of 40 different types of pathogens were examined. Each type of infection has a signature that distinguishes it from people without the infection and from other types of infection. Immunosignature by measuring the antibody response against pathogens, can distinguish bacterial from viral infections. Further, the applicant was able to identify 2 peptides that can distinguish the two classes, which would yield a biomarker with more clinical utility. Further, immunosignature can distinguish bacterial from generally a non-bacterial infection, which also has clinical relevance, since there are always non-bacterial and non-viral infections present in clinical settings.

Pooled materials were examined for common immunosignatures between 4 different bacteria and 5 different viruses, in total 280 samples. Immunosignatures (IMS) are patterns of antibody binding on 125,000 peptide feature chips. The peptides are chosen from random peptide sequence space to maximize chemical diversity for discriminating antibody binding. Immunosignatures have been demonstrated to readily distinguish different types of infections and chronic diseases. A training set of x samples of bacteria, viral and non-infected were used to establish the signature. The training set was validated on an independent set of samples and then tested on another completely independent set. A set of 1000 peptides were identified that could make the distinction with X specificity and Y sensitivity in the test set. Most of the misclassifications were influenza samples called as bacterial infections. To further explore the limits of IMS we included samples from 3 eukaryotic pathogens. While the ability to distinguish all 3 classes decreased in accuracy, the accuracy of distinguishing bacterial from virus and eukaryotic pathogen increased. To examine the issue of whether a lesser number of peptides could distinguish bacterial from viral infection, each peptide was tested for performance. We determined that two peptides performed as well as the 1000 in making the bacteria versus virus call. These two peptides contained motifs that were common in bacterial proteomes. We used the natural bacterial peptides in a simple spot assay to test bacterial and viral sera samples and demonstrated preliminary distinction of the samples.

The sera samples used are listed in Table 1. The term "sample" includes any biological specimen obtained from an individual. Suitable samples for use in the present invention include, without limitation, whole blood, plasma, serum, saliva, urine, stool (i.e., feces), tears, and any other bodily fluid, or a tissue sample (i.e., biopsy) such as a small intestine or colon sample, and cellular extracts thereof (e.g., red blood cellular extract). In a preferred embodiment, the sample is a blood, plasma, or serum sample. In a more preferred embodiment, the sample is a serum sample. They represent a wide range of bacterial and virus species. There were between 9-22 sera samples from each type of pathogen. Each sample was run in duplicate on the standard CIMV7 arrays containing 125K peptides. The process has been described, but briefly, involves diluting the sample 600× in buffer, applying it to the array for one hour, washing and then detecting the pattern of antibody binding with a labeled secondary. In the assays reported here, IgG was detected.

TABLE 1

Sample information used in this application. 12 classes of infections are included in addition to a group of non-infected individuals coded as normal.

| Class of infection | type of infection | sample number | Count per class |
|---|---|---|---|
| non-infected | non-infected | 62 | 62 |
| Bacteria | Borrelia | 9 | 64 |
| Bacteria | Lyme | 13 | |
| Bacteria | Syphillis | 22 | |
| Bacteria | Tuberculosis | 20 | |
| Virus | Dengue | 22 | 105 |
| Virus | Flu | 22 | |
| Virus | Hepatitis B | 20 | |
| Virus | HIV | 21 | |
| Virus | WNV | 20 | |
| Other | Chagas | 19 | 57 |
| Other | Malaria | 17 | |
| Other | Valley Fever | 21 | |

Figure 4:
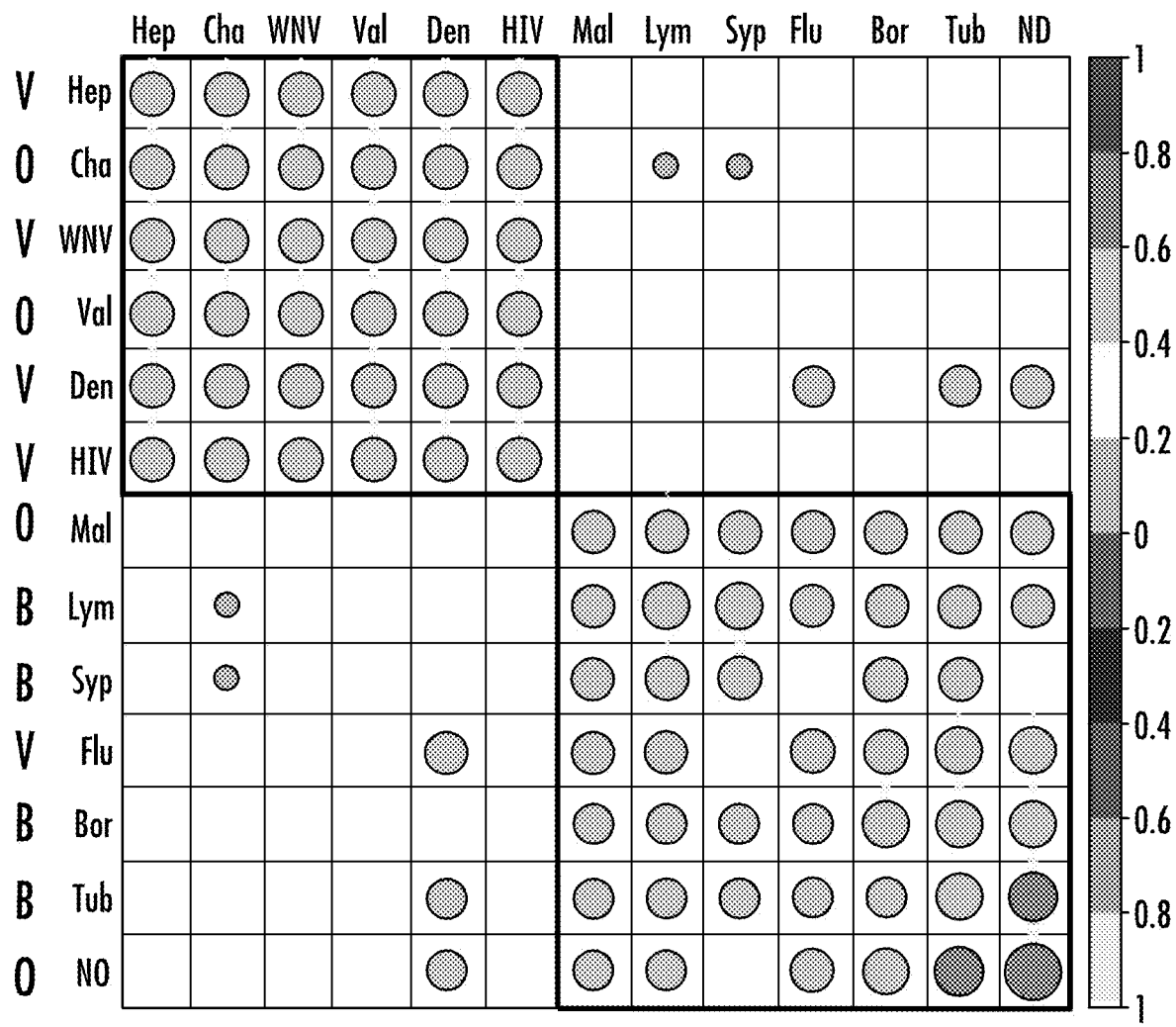
FIG. 4. Hierarchical clustering for the correlation of the whole immunosignature by type of infection including all classes. Non-infected class is more similar to bacterial infection, while the non-bacterial and non-viral infections are spread out in groups.

If the immune system responds to bacterial and viral infections differently, a high correlation for the immune responses within each group and low correlation between them is expected. Correlation is calculated for each pairwise sample comparison with the 125 k features on the immunosignature, then the samples belong to the same class are averaged to a single correlation value (FIG. 1). For example, correlations for all comparisons between any Dengue samples versus any WNV samples are averaged into a single value, representing the average correlation between the two groups. Hierarchical clustering results show bacteria and virus are separated, with the only exception of influenza virus, which is classified with bacteria. FIG. 1 demonstrates the initial unsupervised division showing that influenza virus is the sole misclassified group, classified with bacteria. Given the fact that there is a lot of noise in the immune system and numerous irrelevant antibodies circulating in the blood, this performance exceeds expectation and confirms the hypothesis that the immune system is able to distinguish bacterial and viral infections by producing different antibodies. Non-infected samples and non-bacterial non-viral pathogens are mixed when including them in the correlation table (FIG. 4).

Figure 6:
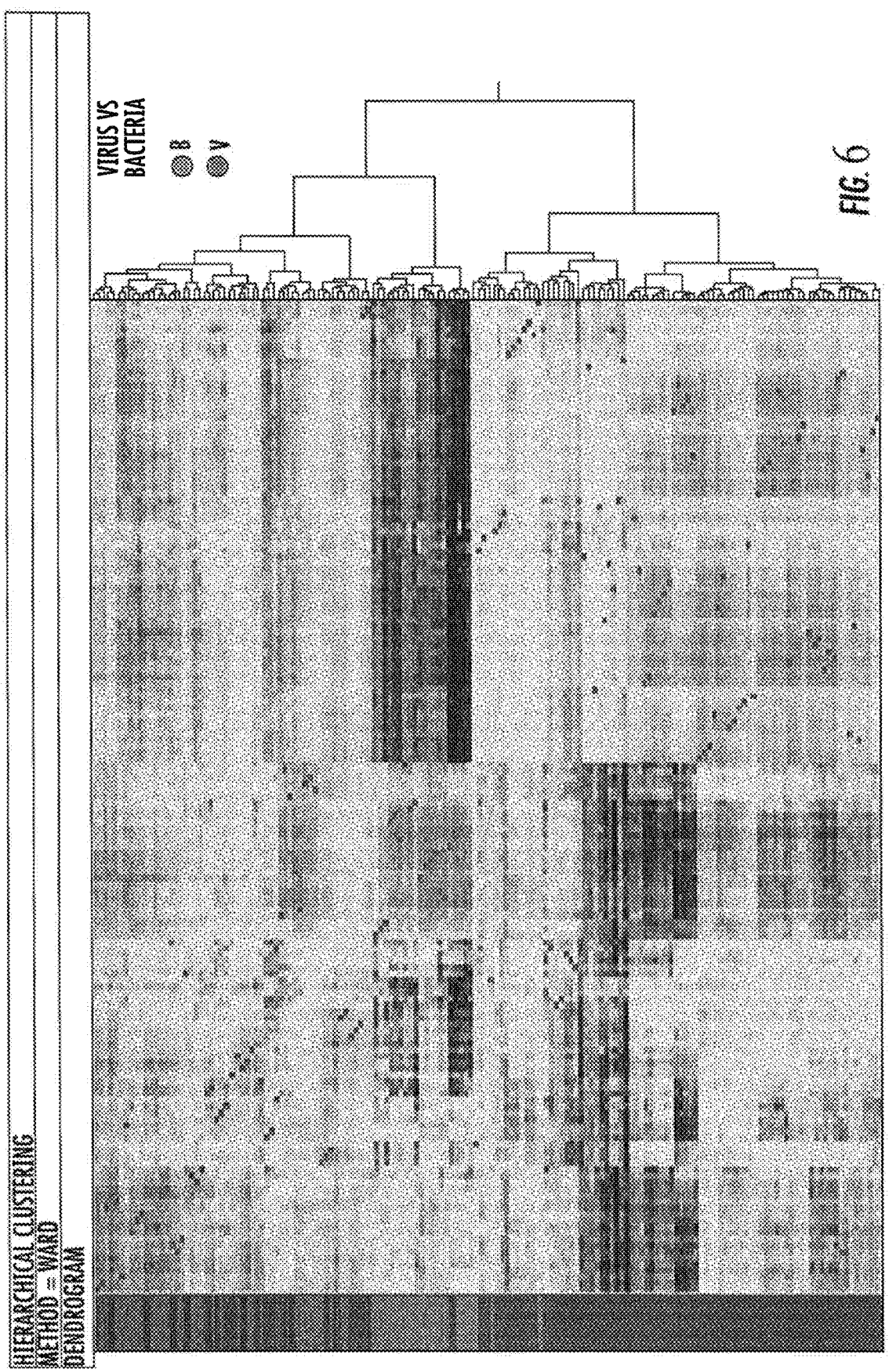
FIG. 6. Hierarchical clustering for the correlation of the whole immunosignature of each sample within bacterial and viral infections. More virus samples are misclassified as bacteria and mostly are influenza samples. Specificity for virus is nearly 100%.

A further breakdown per samples is shown in FIG. 6. Hierarchical clustering using the correlations for every sample (no sample is averaged) is shown in FIG. 6. The specificity for viral infections is close to 100%, with some viruses being classified as bacteria, mostly influenza. This result is consistent with the class level clustering result.

Figure 3:
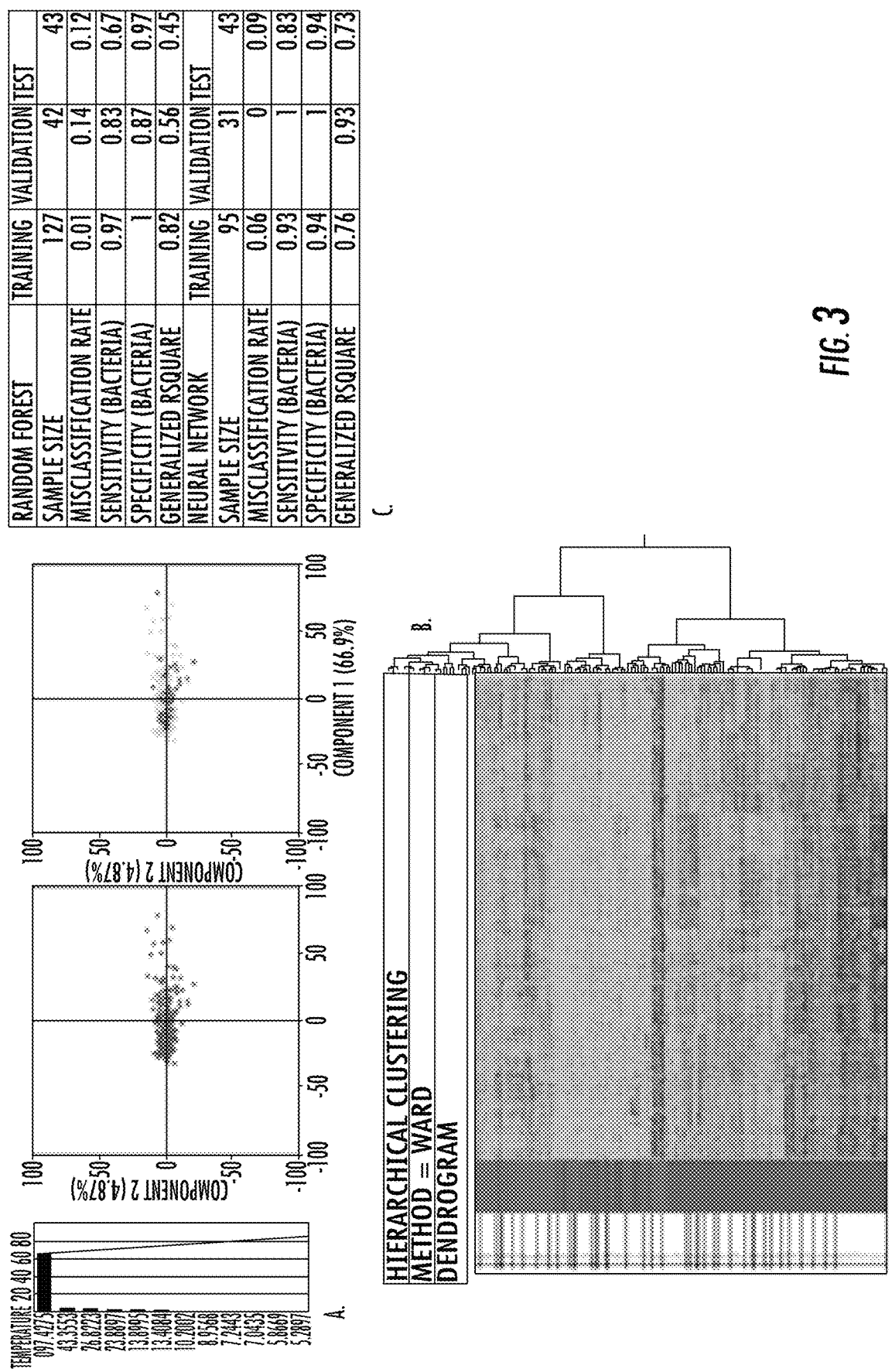
FIG. 3. Performance of distinguishing bacterial versus viral and other types of infection. (a). PCA analysis on the selected peptides shows one factor is responsible for most variability, test set samples are highlighted in the right figure. (b). Clustering of the selected peptides shows most peptides are bacteria specific peptides. (c) Performance of the classification algorithms.

Since samples in one class are merged, performance of each sample is determined. Hierarchical clustering for the correlation table for every sample is shown in FIG. 3a. And the specificity for virus is close to 100%, with some viruses being classified as bacteria, mostly influenza viruses. This result is consistent with the per-class clustering result.

EXAMPLES

Example 1—Building Bacterial Versus Viral Infection Classifier that Shows Robust Distinction Once the viability of distinguishing the two types of infections was confirmed, we utilized machine learning techniques to classify the samples. In this experiment, only bacterial and viral infection samples are used, with a total of 157 samples. Experimental workflow is outlined in FIG. 7. All samples are randomly divided into training, validation and held-out test set, with a ratio of 60%, 20%, 20%. Training and validation sets are used to build the classifier. Test sets remains untouched until the final model is constructed and used only for evaluation.

Since there are 125,000 features on immunosignature platform, it is plausible to first do feature selection to find the most useful peptides and remove noise. Feature selection is performed using training and validation set data via two-tail t-test for every peptide and top 1000 significant peptides are used. Note that the general cutoff is either selecting top 1000 peptides or p-value<$1/125,000$, controlling overall false positive sample to be less than 1. Whichever cutoff has smaller peptide numbers is used in the experiment. For tests we performed, the p-values are much lower than $1/125,000$. As a result, a common cutoff of the top 1000 peptides is used throughout the application. In certain embodiments, the diagnostic peptides are chosen against a background of non-diagnostic peptides on the arrays. In order to provide the non-specific binding buffer to increase specificity, the diagnostic peptides can be arrayed with a set of 100-10,000 random peptides. These could be mixed or individual and spotted separately or as a mixture.

Figure 2:
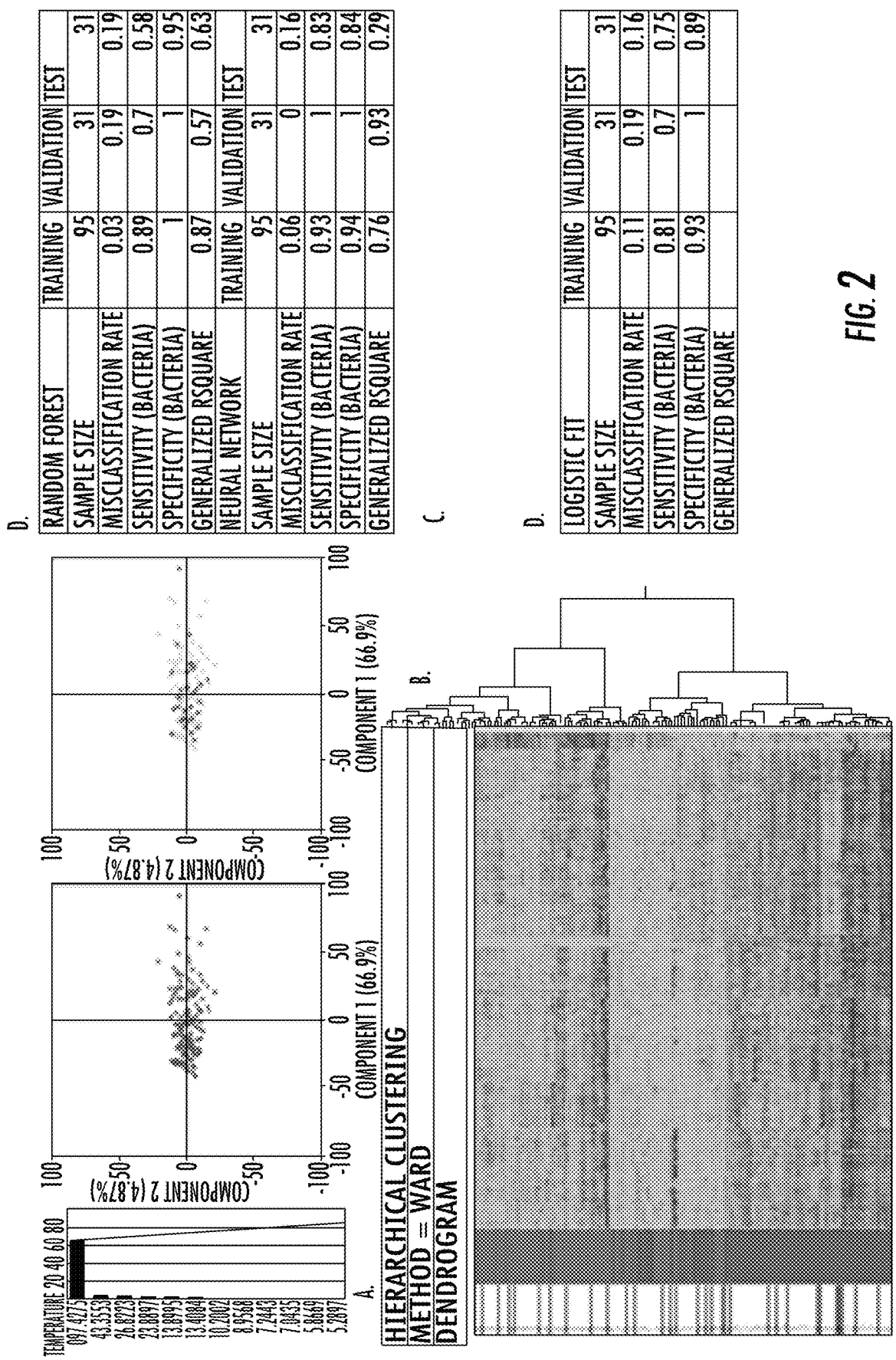
FIG. 2. Performance of distinguishing bacterial versus viral infection. (a). PCA analysis on the selected peptides shows one factor is responsible for most variability, test set samples are highlighted in the right figure. (b). Clustering of the selected peptides shows most peptides are bacteria specific peptides. (c) Performance of the classification algorithms. (d) Two selected peptides can achieve similar performance of classification.

Using the selected features, Principle Component Analysis (PCA) is performed to determine how many components are responsible for the majority of the variability (FIG. 2a). Interestingly, it was found that component 1 alone explains over 60% of the variability, indicating at least one factor is strongly driving the variance across groups, at least for the selected features. The test samples are not used in feature selection, however, when analyzed with PCA (highlighted in FIG. 2a) the test set samples are well separated at the validation set would suggest, suggesting overfitting is negligible. Hierarchical clustering is performed using the selected features to visualize the data (FIG. 2b). As we can see most peptides are relatively higher in intensity in bacterial than viral infections. This suggests the peptides that are being selected are from antibody response were raised to the bacterial infection. The test set samples are also highlighted in the clustering heatmap to show their clustering group location compared with the training and validation set. No obvious overfitting is noted as test set samples are generally clustered in the right class.

Machine learning classifiers like Random Forest and Neural Networks are used to build the model of classification between the two groups. For each classifier, a model is trained using training data and a validation set is used to fine-tune the model and gain an initial performance evaluation to limit overfitting. After the established model is used on the test set, we perform a final performance evaluation on this independent dataset. Experiments with training group only usually results in overfitting because the classifier might adjust to the random variations in the training group to gain best fit scores. Validation set only also pose the same issue because the model is generated with information from the validation dataset. In microarray studies, there are inevitably more variables than observations, overfitting becomes more pronounced. Independent datasets are needed to test the performance of the classifier, the test set data are never used in feature selection to model generating and is only used for the final evaluation of the model.

Figure 8:
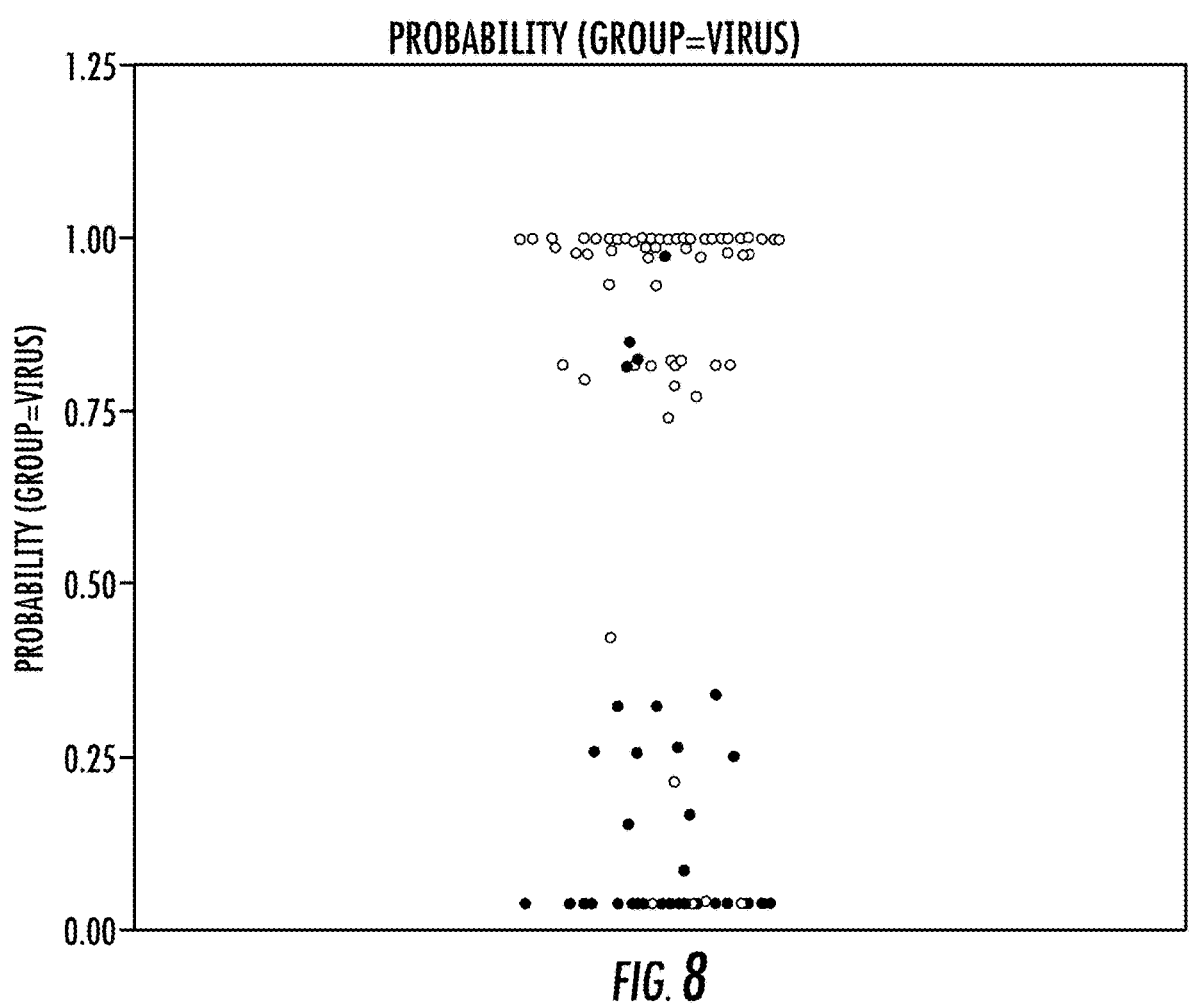
FIG. 8. Probability graph for being virus using Neural Network method in bacteria vs viral infection experiment.

As it is shown in FIG. 2c, Random Forest and Neural Networks both have minimal misclassification rate on both training and validation. The final performance on the test set is also similar for both classifiers. Random Forest tends to exhibit less sensitivity to the bacterial infections (sensitivity at 0.58) but is extremely specific (0.95). This is a bias toward true negatives as the cost of lower true positives. Neural Network models yielded more balance for TP and FP between the two groups, with sensitivity and specificity at 0.83 and 0.84 respectively (FIG. 8). Both models yield misclassification rates of less than 20%. Since it may be that up to 60% of human infections are from virus, if doctors can distinguish viral infections from bacterial infections, the use of antibiotics could be reduced by over 50%.

Figure 5:
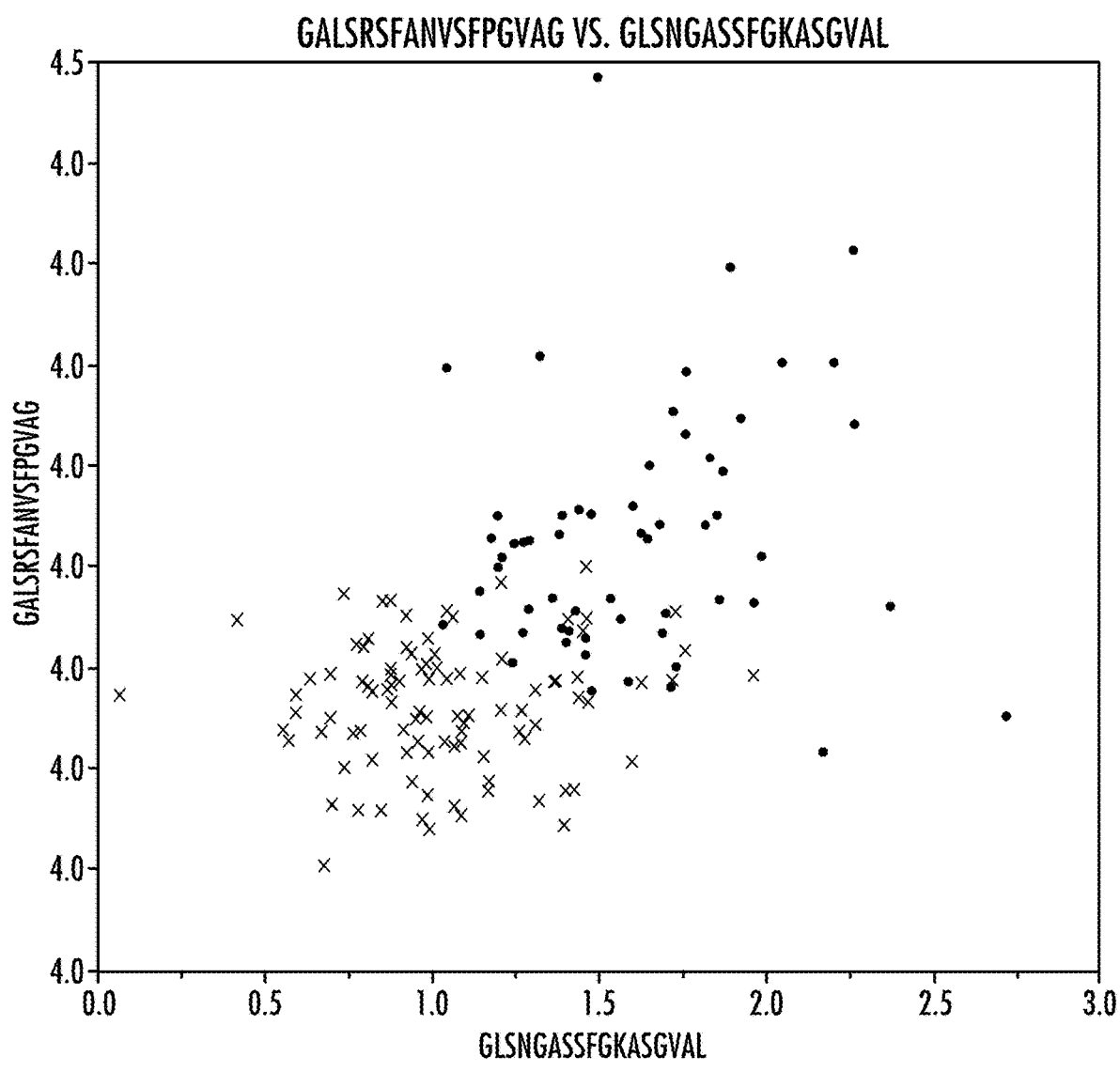
FIG. 5. Scatterplot of the 2 selected peptides. Color is true class. All samples are included in this figure. Both peptides are bacteria specific peptides.

Stepwise regression is utilized to find the optimal, non-redundant peptides that can be used to fit the model. Each peptide has to meet a p-value cutoff of 0.1 to enter the model and will exit the model upon the exceeding the existing cutoff p-value of 0.1. Regression is started assuming all peptides are out of the model. The whole process is iterated until the model is stabilized, meaning, i.e., no peptides leave or enter the model. Then the model is fine-tuned to maximize RSquare for the Validation set (FIG. 2d). The final model only includes two peptides, GALSRSFANVSFPGVAG (SEQ ID. No. 1) and GLSNGASSFGKASGVAL (SEQ ID. NO. 2) (FIG. 5). Specificity and sensitivity for the test set comes to 0.75 and 0.89, only marginally worse than the complete models using all 1000 peptides. And the misclassification rate is at 0.16, no worse than the complete models.

Upon performing blast search on these 2 peptides against the RefSeq database excluding *Homo sapiens*, Models (XM/XP) and Uncultured/environmental sample sequences, they were found to be highly enriched in bacteria but not in virus (FIG. 4). Furthermore, they are prevalent in all types of bacteria and all types of proteins, suggesting they are indeed good bacterial infection detection molecules/biomarkers.

TABLE 2

Performance of bacterial vs non-bacterial infection classification using 5 selected peptides. Peptides are selected from stepwise regression using mixed p-value model at cutoff of 0.1. Logistic fit is then performed using the selected peptides. Test set performance is much lower compared with the complete model using all selected peptides from T-Test.

| logistic Fit | Training | Validation | Test |
|---|---|---|---|
| Sample size | 127 | 42 | 43 |
| Misclassification rate | 0.06 | 0.14 | 0.23 |

TABLE 2-continued

Performance of bacterial vs non-bacterial infection classification using 5 selected peptides. Peptides are selected from stepwise regression using mixed p-value model at cutoff of 0.1. Logistic fit is then performed using the selected peptides. Test set performance is much lower compared with the complete model using all selected peptides from T-Test.

| logistic Fit | Training | Validation | Test |
|---|---|---|---|
| sensitivity(Bacteria) | 0.89 | 0.58 | 0.45 |
| Specificity(Bacteria) | 0.96 | 0.97 | 0.875 |

Example 2—Epitopes of Bacteria were Identified Via Blast Search of the Two Peptides Followed by Ungapped Motif Mapping Epitopes within the two peptides were examined. The two peptides may contain bacterial epitopes or mimotopes that enhance bacteria-specific antibody binding. We then did a protein blastp search of the 2 peptides against the Bacteria (taxid:2) with no E-value cutoff. One hundred matched sequences in bacteria proteomes were identified and subsequently submitted to the MEME tool in the MEME suite to identify consensus motifs. The identified motif(s) are the epitope(s) from bacteria that the 2 peptides represent. Results are shown in table 3. One epitope (SEQ ID No. 3) is identified for peptide 1 (SEQ ID No. 1); and two epitopes (SEQ ID No. 4 and SEQ ID No. 5) were identified for peptide 2 (SEQ ID No. 2). It is interesting to note that for peptide 1 (SEQ ID No. 1), only 6 amino acids seem to be the target of bacterial specific antibodies. As for peptide 2 (SEQ ID No. 2), the full length of the peptide could be the target of bacterial specific antibodies. Each epitope is matched with at least 20 sequences from the bacterial proteome, so the epitopes are broadly represented in the bacterial world.

TABLE 3

Identified epitopes of bacteria with the 2 bacterial-viral distinguishing peptides. Peptide 1 (SEQ ID No. 1) has 1 epitope (SEQ ID No. 3) with length of 6 amino acid (a.a). While peptide 2 (SEQ ID No. 2) has 2 matched epitopes (SEQ ID No. 4 and SEQ ID No. 5) with length of 8 a.a. and 6 a.a. correspondingly. Matched part is highlighted with color in peptides. This implies only part of peptide 1 is identified by bacterial specific antibody while the whole sequence of peptide 2 is the target for bacterial antibodies.

| | epitope 1 | epitope 2 |
|---|---|---|
| GALSRSFANVSFPGVAG (SEQ ID No. 1) | RSFANV (SEQ ID No. 3) | |
| GLSNGASSFGKASGVAL (SEQ ID No. 2) | SFGKASGV (SEQ ID No. 4) | LSNGAS (SEQ ID No. 5) |

Example 3—Broad Bacterial Versus Non-Bacterial Infection Classifier Shows Robust Distinction and Better Performance In clinical settings, it is possible that one will encounter nonbacterial or non-viral infections, so the ability to distinguish the other types of infections is important in doing a correct diagnosis. Thus, the focus is on binary classification of bacterial vs non-bacterial infections, because patients with bacterial infection can immediately receive antibiotics as treatment while other infections need more detail to arrive at a disease specific treatment. Accordingly, for example, Chagas, malaria and Valley Fever are included as noise and combined with viral infections as the non-bacterial infection class.

Figure 7:
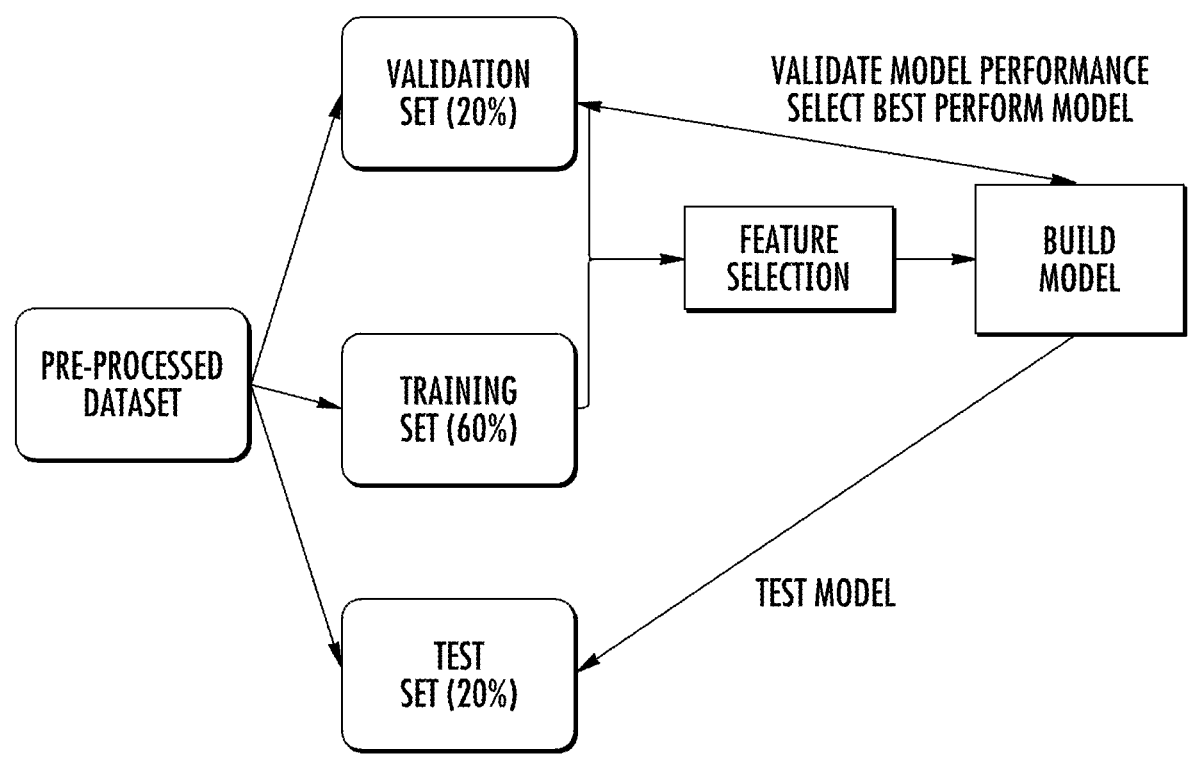
FIG. 7. Hierarchical clustering for the correlation of the whole immunosignature of each sample within bacterial and viral infections. More virus samples are misclassified as bacteria and mostly are influenza samples. Specificity for virus is nearly 100%.

Experiments were performed as described in FIG. 7, samples are divided into training, validation and test set. Training and validation set are used to do feature selection and construct a model, then performance is tested on the independent test set. Results were summarized in FIGS. 3a-3c. PCA analysis (FIG. 3a) and hierarchical clustering (FIG. 3b) show similar separation of the two group like FIGS. 2a-2d, suggesting performance does not deteriorate when noise is added. Random Forest model and Neural Network model revealed a misclassification rate of 0.12 and 0.09 for the test set, which is an improvement compared with the bacterial vs viral only model. The better performing Neural Network model is at 0.83 sensitivity and 0.94 specificity for bacteria with a Generalized RSquare of 0.73, all of which is a significant increase compared to the original bacterial vs viral model. This improvement can be the result of more samples being used for model construction, or it can be by including more types of infection as the non-bacteria comparison, which can lead to a more robust bacterial specific signature.

In this experiment, we also attempted to find minimal number of peptides that can achieve similar performance compared with using all selected peptides. However, after the same stepwise regression process, the best performance we can get is using 5 peptides to gain a misclassification rate of 0.23, which is not as good as the complete model using all 1000 peptides. Also, the sensitivity for bacteria only was 0.44, also significantly lower than the Neural Network model.

DISCUSSION

Immunosignature, a microarray-based serological test that uses semi-random peptides to splay out the antibody repertoire from infected individuals, is used to distinguish viral infections from bacterial infections. Immunosignatures can detect peptides that generally separate bacterial infections from viral infections. Machine learning models were used to identify the predictive performance of a given set of peptides across 169 patients, of which 105 patients have bacterial infections and 64 viral infections. We achieved over 84% accuracy, 84% specificity, and 83% sensitivity, and could achieve similar accuracy, specificity, and sensitivity with as few as two peptides. These two peptides were overrepresented in bacterial proteomes, and underrepresented in viral proteomes. Even when adding fungal and protozoan infections, high specificity is maintained, an important goal to achieve when attempting to reduce improperly prescribed antibiotics.

Accurate diagnosis of bacterial and viral infections is needed in clinical settings. The current imprecise diagnosis results in either over use of antibiotics or delayed treatment for patients. Herein is a novel diagnosis based on immunosignature technology that is able to reliably diagnose bacterial infection from viral infections. By measuring the antibody response of patients with different infections, the ability to distinguish the majority of the bacterial and viral infections has been demonstrated. We further construct models based on selected features and applying machine learning algorithms to the selected features. This model is able to classify the two types of infections with misclassification rate of less than 20%, exceeding current methods used either in research or clinical settings. Since in clinical settings non-bacterial, non-viral infections will be expected, we also constructed a model aimed at distinguishing bacterial versus all other non-bacterial infections, consisting of viral infection and noise infections including Chagas, Malaria and Valley Fever. This model shows even better performance with misclassification rate at about 10%.

Several studies using gene expression profiling have shown potential to diagnose of bacterial vs viral infections. The logic behind those studies is genes will be differentially regulated when encountering different infections. So is it the case for antibody response. Antibody response is the most direct reaction for an infection. Given the fact that genes as indirect reactions can still work to distinguish infections types, antibody response should be an even better approach because of it directly targeting the pathogens. One thing worth noting is that compared with gene microarrays, where it is usually one-to-one binding, antibodies will usually bind to multiple peptides on an immunosignature platform as long as the peptides are mimotopes of the true epitope. As a result, more peptides are used in analysis for the immunosignature experiments.

Correlation of the infections are used to first test the possibility of distinction at the antibody system level. The logic behind using correlation of infections is that the immune system might systematically see the difference between bacterial and viral infection by activating different pathways. Immunosignature platforms measure antibody repertoire in the blood. If you use all the data from the platform, then you are measuring the immune system. Correlation of the immune system can then be tested by calculating the correlation of the immunosignature for different pathogens. The result from the correlation offer insights into understanding both diagnosis and how the immune system works. It seems the immune system is able to distinguish most bacterial and viral infections and mount totally different immune response, since only one infection is misclassified. This confirms the notion that our immune system probably knows the source of the infection and respond accordingly. Or perhaps the immune system does not know the source of infection but because all infections within the same class are so similar, the immune system always produces similar antibodies against various bacterial infections. The same might be the case for viral infection. As discussed above, most of the signatures that can distinguish bacterial and viral infection are bacterial specific signatures, implying the immune system is producing various antibodies against bacterial infection in ways analogous to broad-spectrum antibiotics.

And the result that influenza virus is misclassified into bacteria is interesting because it suggests somehow influenza virus successfully tricked the immune system into thinking it is bacteria such that antibodies against bacteria are produced, the result of which will be ineffective. This is consistent with the fact that viruses are highly contagious worldwide, implying the immune system cannot quickly mount an effective immune response because influenza virus is regarded as "bacteria." This misclassification by the immune system might also explain why there are already pre-existing neutralizing antibodies within the immune system, but they were not usually elucidated during flu infection.

Overfitting has been a major problem in microarray studies. Here we approach the experiments with a pre-isolated test set data to avoid the problem. The whole model construction process is without information from the test set. After the model is stabilized, its performance is tested with the test set data. And the results show there is little overfitting when migrating the model from the training, validation set to the test set.

In the bacterial versus viral infection model, we are achieving accuracy of over 80% in both classifiers tested. And clinicians can choose which classifier to use based on experience, since following the random forest classifier will minimize the diagnosis of viral infection into bacterial infection, hence lower the usage of anti-biotics, while the neural network classifier tends to balance the error rate in each class, resulting in more usage of antibiotics but less suffering of patients who genuinely have a bacterial infection. Features being selected from this study are almost exclusively from bacterial infection, indicating there is more commonality with the immune response.

The two peptides were further examined by identifying matched sequences from bacteria proteomes and then identifying consensus motifs with the matched sequences. These consensus motifs could be the binding target within the two peptides on the immunosignature. Only 6 a.a. of consensus motif in one of the peptides is identified and the full length of the other peptide is matched by bacterial antibodies. This indicates there could be redundancy in these two peptides.

Interestingly, when non-bacterial and non-viral infections are added as the non-bacterial class, the performance of the model actually increases. Accuracy is at ~90% in both classifiers. And specificity for Bacteria it is ~95% in both classifiers, indicating this model is good at distinguishing non-bacterial infections. When coupled with the results of the clustering heatmap, it appears that our immune system sees the commonality for bacterial infections but not other types. This is interpreted from the classifier result that all features are bacteria specific features and as long as you don't have those features, you are classified into the non-bacterial class.

In summary, we are able to construct classifiers that are better performing for bacterial versus viral infection. We validated each model using independent dataset to confirm the robustness of the model. And we are able to confirm the source of the selected features, which in turn offers the logic for the success of the model. We believe immunosignatures can be beneficial when used in clinical settings to both combat the antibiotic overdose problem and to reduce suffering of the patients. In other words, a patient whose antibody-containing sample binds to one or more peptides indicating a bacterial infection can be treated with antibiotics, while a patient whose antibody-containing sample binds to one or more peptides on the array indicating a viral infection can be treated with an anti-viral medicament, such as nitazoxanide.

Materials and Methods
Study Design

Serum samples were collected at various source described in detail below and received at Arizona State University (ASU) under Institutional Review Board Protocol #0912004625, "Profiling Serum for Unique Antibody Signatures". All samples have informed consent and were anonymized. Every disease sample was tested positive for the specified disease before rendering to ASU. *Bordetella pertussis* samples were provided by Seracare Life Sciences (Seracare). Tuberculosis from University of Texas at El Paso (UTEP). Malaria from Seracare. HIV from Creative Testing Solutions (CTS). Flu from BioreclamationIVT. Dengue from UTEP. WNV from CTS. VF from Sonora Lab. Chagas from CTS. Lyme from Seracare. Hepatitis B from CTS, Syphilis from Seracare.

*Bordetella pertussis*, Lyme, Syphillis, Tuberculosis, Dengue, Flu, Hepatitis B, HIV and WNV samples are used in the bacterial versus viral experiment. Chagas, Malaria and Valley Fever were added in the bacterial versus non-bacterial experiment. All samples are randomly assigned into training, validation and test set with equal probability.

Immunosignature Assay

Serum samples were diluted 1:1500 into the sample buffer (3% BSA in 1× PBST) before incubated on immunosignature microarrays at a final volume of 150 ul for 1 h at 37° C. with rotating. Primary antibodies from the serum were then washed with 1×PBST for 3 times and rinsed with $ddH_2O$ for 3 times. 4 nM Secondary anti-human IgG antibodies with Alexa-Fluor 555 conjugation from Life Technologies are added in secondary incubation buffer (0.75% Casein in 1×PBST with 0.05% Tween20) to detect primary antibody binding. Secondary antibodies were incubated on the array for 1 h at 37° C. before washed off with blocking buffer. Slides were then washed with 1× PBST and $ddH_2O$ before drying. Images were obtained from scanning arrays at 555 nm using Innoscan 910 scanner. Signal intensity for features were extracted using GenePix Pro 6.0.

Statistical Analysis

Analysis is performed using scripts written in R or the JMP software (SAS Institute Inc.). Raw intensity reads for all samples are normalized to the median per sample. Quality Control (QC) for the samples is performed by checking each sample's average correlation against all other samples. Samples with correlation<0.2 are deleted. 226 samples are run on immunosignature and 212 samples passed QC and were analyzed.

Feature selection is done by using samples in the training and validation set. Two-tail Student's T-Test is performed for each peptides by comparing bacterial infection samples versus viral infection samples (non-bacterial infection samples). Cutoff is controlled at allowing 1 false positive for all test, which is 1/124,000 or 1000 peptides, whichever is smaller.

PCA is performed using selected peptides with all samples, with the test set samples highlighted in right PCA plot. Hierarchical clustering is performed using the selected peptides with all samples. Ward method is used in calculating the distance between the samples. The same method is used in calculating distance for the features in two-way clustering.

Random Forest is carried out with maximum 100 trees in the forest. Minimum split per tree is set at 10 and maximum at 2000. Early stopping rule is applied on validation set. And performance of the classifier is evaluated and output as confusion matrix for the training, validation and test set. Neural Network is built with one hidden layer and 3 nodes, with TanH as the activation function.

Stepwise regression for reducing number of features is used with stopping rule of p-value cutoff at 0.1 for both entering and leaving the model. The model starts empty with no feature. Features become included in the model if below cutoff p-value and will be removed from the model once p-value larger than the cutoff. This process is done recursively until the model stabilize, with no feature entering and leaving the model. Then the selected features are tuned to maximum RSquare for the validation set. Then Logistic regression is used in building model with the 2 selected peptides.

Blast search of the 2 peptides is done using the NCBI blast server. Protein Blast (blastp) suite is used. Database is Reference proteins and organism is limited to Bacteria (taxid:2). Algorithm parameters is set to adjust for short sequences, and max target sequences at 100. Then the matched sequences are processed to contain only linear matched part. The 100 matched sequences are imported into MEME suite to identify epitopes, with configurations of 10 minimum sites per epitope and 3 maximum epitopes.

While the preferred embodiments have been illustrated in detail, it should be apparent that modifications and adaptations to those embodiments may occur to one skilled in the art without departing from the scope of the present claims.

What is claimed is:

1. A method to distinguish a bacterial infection from a viral infection, the method comprising:
   contacting an antibody-containing sample with an array of immobilized peptides, wherein said peptides are selected from a group consisting of one or more peptides that bind to antibodies produced in response to a bacterial infection and one or more peptides that bind to antibodies produced in response to a viral infection, wherein the array of immobilized peptides comprises SEQ ID NO: 1 and SEQ ID NO: 2; and
   detecting binding of an antibody from said sample with a peptide from said group.

2. The method of claim 1, wherein the array of immobilized peptides comprises at least 125,000 different peptides.

3. The method of claim 1, wherein the array of immobilized peptides comprises at least 1,000 different peptides.

4. The method of claim 1, wherein SEQ ID NO: 1 comprises a motif able to bind to one or more antibodies produced in response to a bacterial infection and the motif comprises SEQ ID NO: 3.

5. The method of claim 1, wherein SEQ ID NO: 2 comprises a first motif and a second motif able to bind to one or more antibodies produced in response to a bacterial infection, wherein the first motif comprises SEQ ID NO: 4 and the second motif comprises SEQ ID NO: 5.

6. The method of claim 1, wherein said immobilized peptides are selected using a two-tail t-test result having a p-value less than $1/125{,}000$.

7. The method of claim 1, wherein said antibodies produced in response to a bacterial infection and said antibodies produced in response to a viral infection are human antibodies.

8. The method of claim 1, wherein the sample is a blood or serum sample.

9. The method of claim 1, further including the step of treating a patient with a bacterial infection with antibiotics.

10. The method of claim 1, further including the step of treating a patient with a viral infection with an anti-viral medicament.

11. The method of claim 1, wherein the array of immobilized peptides comprises one or more peptides that bind to antibodies produced in response to a bacterial infection, one or more peptides that bind to antibodies produced in response to a viral infection, and one or more peptides that do not bind to antibodies produced in response either to a bacterial infection or to a viral infection.

12. The method of claim 10, wherein the anti-viral medicament is nitazoxanide.

13. The method of claim 1, wherein the bacterial infection is a *Bordetella pertussis, Borrelia*, Lyme, Syphilis, or Tuberculosis infection.

14. The method of claim 1, wherein the viral infection is a Dengue, Flu, Hepatitis B, HIV, or WNV infection.

15. The method of claim 1, wherein the sample is a plasma sample.

16. The method of claim 1, wherein detecting binding of an antibody comprises incubating with a secondary antibody.

17. The method of claim 1, wherein the antibody-containing sample is contacted with an array of immobilized peptides for one hour.

18. The method of claim 1, wherein contacting an antibody-containing sample with an array of immobilized peptides is performed in duplicate.

19. The method of claim 1, wherein the antibody from said sample is an IgG antibody.

20. The method of claim 1, wherein said sample is from a patient experiencing a respiratory tract infection or pediatric sepsis.

* * * * *